(12) United States Patent
Takahashi et al.

(10) Patent No.: US 7,598,090 B2
(45) Date of Patent: *Oct. 6, 2009

(54) BIOSENSOR

(75) Inventors: Mie Takahashi, Niihama (JP);
Masataka Nadaoka, Iyo (JP); Hirotaka Tanaka, Ehime (JP); Fumihisa Kitawaki, Kadoma (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/492,011

(22) Filed: Jul. 24, 2006

(65) Prior Publication Data

US 2006/0275921 A1    Dec. 7, 2006

Related U.S. Application Data

(62) Division of application No. 10/069,845, filed on Jun. 5, 2002, now Pat. No. 7,112,451.

(30) Foreign Application Priority Data

Jun. 28, 2000  (JP) .............................. 2000-194183
Jun. 28, 2001  (WO) ...................... PCT/JP01/05561

(51) Int. Cl.
*G01N 33/53* (2006.01)
(52) U.S. Cl. ...................... 436/514; 436/518; 436/810; 435/7.1; 435/7.94; 435/287.1; 435/287.2; 435/287.3; 435/287.7; 435/805; 435/810; 435/970; 422/56; 422/57; 422/59; 422/60
(58) Field of Classification Search ................. 436/514, 436/518, 810; 435/4, 7.1, 7.94, 287.1, 287.2, 435/287.3, 387.7, 805, 810, 970, 187.2, 287.7; 422/56–60
See application file for complete search history.

(56) References Cited

U.S. PATENT DOCUMENTS 4,477,575 A   10/1984  Vogel et al.

(Continued)

FOREIGN PATENT DOCUMENTS

EP            0 785 430 A1      7/1997

(Continued)

OTHER PUBLICATIONS

Metzner W., et al: "A Method to Biotinylate and Histochemically Visualize Ibotenic Acid for Pharmacological Inactivation Studies," Journal of Neuroscience Methods, Elsevier Science Publisher B. V., Amsterdam, NL, vol. 76, No. 2, Oct. 3, 1997, pp. 143-150.

(Continued)

*Primary Examiner*—Bao-Thuy L Nguyen
(74) *Attorney, Agent, or Firm*—Marjama Muldoon Blasiak & Sullivan LLP

(57) ABSTRACT

A biosensor is provided with an area in which a reagent having bleaching action is carried in a state where it can be dissolved, at least in a part of a sample application area to which an inspection target solution is applied or the downstream of the sample application area in the direction of the inspection target solution permeating, in a development layer. In the so-constituted biosensor, a colored component in the inspection target solution can be faded by the bleaching reagent, so that the color in parts other than a reactive area is reduced in consequence, whereby a visual judgment is possible and a more accurate measurement result in which a reading error by a measuring device is extremely suppressed can be obtained.

15 Claims, 10 Drawing Sheets

U.S. PATENT DOCUMENTS

| | | | |
|---|---|---|---|
| 4,816,224 A | | 3/1989 | Vogel et al. |
| 5,166,051 A | * | 11/1992 | Killeen et al. ............ 435/7.1 |
| 5,728,587 A | * | 3/1998 | Kang et al. ............ 436/518 |
| 6,008,059 A | | 12/1999 | Schrier et al. |
| 6,040,195 A | | 3/2000 | Carroll et al. |
| 6,069,014 A | | 5/2000 | Schrier et al. |
| 6,197,598 B1 | | 3/2001 | Schrier et al. |
| 6,284,550 B1 | | 9/2001 | Carroll et al. |
| 6,448,062 B1 | * | 9/2002 | Huth et al. ............ 435/264 |
| 6,471,728 B2 | * | 10/2002 | Smith et al. ............ 8/137 |
| 7,112,541 B2 | * | 9/2006 | Xia et al. ............ 438/771 |
| 2002/0137230 A1 | | 9/2002 | Nadaoka et al. |

FOREIGN PATENT DOCUMENTS

| | | |
|---|---|---|
| EP | 832430 | 4/1998 |
| JP | 57-53661 | 3/1982 |
| JP | 09-196908 | 7/1997 |
| JP | 11-505327 | 5/1999 |
| JP | 11505327 | 5/1999 |
| JP | 2003507741 | 2/2003 |
| JP | 2005055451 | 3/2005 |
| JP | 20060177970 | 7/2006 |
| JP | 3831403 | 10/2006 |
| WO | WO 96/35952 | 11/1996 |
| WO | WO-9635952 | 11/1996 |
| WO | WO-0114876 | 3/2001 |

OTHER PUBLICATIONS

Supplementary Search Report for International Patent No. PCT/JP0105561, dated May 2, 2007, 3 pages.

* cited by examiner

BIOSENSOR

This application is a division of application Ser. No. 10/069,845, filed Jun. 5, 2002 now U.S. Pat. No. 7,112,451.

FIELD OF THE INVENTION

The present invention relates to a biosensor and, more particularly, to a biosensor for analyzing constituents of blood.

BACKGROUND OF THE INVENTION

The structure of a conventional biosensor is shown in FIG. 16.

FIG. 16 is a perspective view illustrating the structure of the conventional biosensor test strip.

In FIG. 16, numeral 1 denotes a reactive layer carrier support body composed of a plastic or the like, which supports chromatography materials. Numeral 2 denotes a sample application area composed of a nonwoven fabric or glass fiber filter paper having high absorptivity, or the like, to which an inspection target solution is added or applied, numeral 3 denotes a marker hold region where a marker reagent is held so as to be dissolved, numeral 4 denotes a reactive layer made of nitrocellulose or the like, in which the sample is developed to cause a reaction, numeral 5 denotes a specific protein immobilization part in which a specific protein is immobilized on the region of the reactive later 4, and numeral 6 denotes a water absorbing area which absorbs the inspection target solution finally. The respective regions of the sample application area 2, the marker hold region 3, the reactive layer 4, the specific protein immobilization part 5, and the water absorbing area 6 are formed on the reactive layer carrier support body 1.

An operation of the so-constituted biosensor will be described with reference to FIG. 16.

First, when a liquid sample as an inspection target solution is applied to the sample application area 2, it reaches the area of the marker hold region 3. Then, a marker reagent held in the area of the marker hold region 3 is dissolved due to permeation of the liquid sample and permeates into the region of the reactive layer 4. On the region of the reactive layer 4, there is the specific protein immobilization part 5 in which a specific protein is immobilized, and a reaction is caused between the marker reagent eluted from the area of the marker hold region 3 as well as an analysis target in the liquid sample and the specific protein. At this time, when the analysis target exists in the liquid sample, some color reaction is seen in the region of the specific protein immobilization part 5. The liquid sample is finally absorbed into the water absorbing area 6, and the reaction is ended.

As described above, the biosensor can qualitatively or quantitatively measures components to be measured in a measurement target easily only by the application of the inspection target solution. An example of this biosensor is an immunochromatographic sensor.

A typical immunochromatographic sensor includes an application layer to which the inspection target solution is applied, at least one or plural development layers, and an absorbing layer provided at the end. Further, an antibody immobilization part where an antibody for the measurement target in the inspection target solution is immobilized is provided in a part of the development layer. An antibody for different epitope from the antibody in the antibody immobilization part, which is marked on the upstream side of the antibody immobilization part, is held in a dry state where it can be eluted by the inspection target solution. While mention is made of "different epitope" here, this is not to be regarded as restrictive in a case where an antigen having the identical structure in the identical molecule, such as a dimeric or more antigen, is employed.

Such immunochromatographic sensor has a reaction mode referred to as a sandwich reaction, by which a complex of the antibody immobilized in the antibody immobilization part, the measurement target in the inspection target solution, and the antibody for different epitope from the antibody in the antibody immobilization part is formed.

An operation of the so-constituted immunochromatographic sensor will be described.

First, when a required amount of inspection target solution is applied to the application layer, the inspection target solution permeates into the development layer, and a measurement is started. Then, when the measurement target exists in the inspection target solution, the measurement target can be obtained by the marked antibody bonded to the antibody immobilization part. A typical example of this marked antibody is gold colloid particles, by which visual confirmation is possible, thereby to obtain a measurement result, when the measurement target exists in the antibody immobilization part.

The description has been given here of a case where the sandwich reaction of an antigen antibody reaction, which employs the antibody for the test strip to detect the antigen in the inspection target solution, is taken as a measurement principle. However, the measurement principle is not restricted thereto, and a reaction system in which the antigen is included in the immobilized reagent and the marker reagent to detect the antibody in the inspection target solution may be also employed, and the measurement result can be also obtained by confirming a bonding state of the marker reagent in the antibody immobilization part even when other competitive reactions are similarly taken as measurement principles.

By the way, a biochemical examination of blood is widely implemented as a means for diagnosing the health condition of a person. For example, a measurement of a kind or concentration of a metabolic product, a protein, lipid, an electrolyte, an enzyme, an antigen, an antibody and the like, which are constituents in blood, is performed, while it is hard to perform the measurement directly with whole blood when the above-described immunochromatographic sensor is employed. Generally, to perform the measurement with the whole blood employing the chromatographic sensor, it is required to centrifuge the whole blood first to obtain blood plasma or blood serum as a specimen, and the measurement is performed with the specimen. However, the centrifugation takes labor and time, and thus this chromatographic sensor is unfavorable particularly when a small number of specimens are to be processed immediately or when the examination is to be performed out of doors, at bed side, in the scene of emergency medical care and the like, where facilities for the above operation are not prepared.

In recent years, a quick, simple, accurate, low-cost, and easily available measuring device is desired on the concept of POC (Point of Care) in medical examination scene. The immunochromatographic sensor which can perform a measurement by the application of the inspection target solution is widely utilized for a diagnosis in restricted measurement items and the like as well as in the medical scene owing to its simple measuring operation.

However, according to a biosensor typified by the conventional immunochromatographic sensor, it is difficult to analyze general constituents of blood. That is, for the analysis of the constituents of blood, it is required to centrifuge previously collected blood to obtain blood plasma or blood serum and perform the analysis employing the blood plasma or the blood serum with a large sized analytical instrument. Accordingly, not only a specific machine but also a pretreatment are required for the measurement, so that the examination takes a long time. Therefore, cellular components such as blood corpuscles are affected.

As a method for analyzing constituents of blood with no influence of blood corpuscle components, Japanese Published Patent Applications No. Sho. 57-53661, No. Hei. 8-54387 and No. Hei. 9-196908 disclose a method of filtrating blood corpuscles, by which whole blood is filtrated to separate blood plasma from the whole blood.

For example, according to Japanese Published Patent Applications No. Sho. 57-53661 and No. Hei. 8-54387, to separate blood corpuscle components more completely, glass fiber filter paper with average diameter of 0.2 to 5 μm and density of 0.1 to 0.5 g/cm$^3$ is employed to exude blood, thereby obtaining separated blood plasma and blood serum. However, according to this method, efficiency of blood corpuscle separation is surely enhanced, while it takes quite a long time to almost completely separate the blood corpuscles and a large amount of blood is required to obtain the amount of specimen required for the examination. That is, the amount of blood serum or blood plasma obtained is small with respect to the amount of blood application.

Further, according to Japanese Published Patent Application No. Hei. 9-196908, to prevent clogging in a filtration material due to blood corpuscles and obtain a larger amount of blood plasma or blood serum component from a smaller amount of blood, a water solution of an amino acid or inorganic salt is mixed with whole blood and blood corpuscle components are filtrated thereafter. However, this method requires operations of adding the applying water solution to previously obtained blood and filtrating the blood corpuscle components thereafter, whereby the operation becomes complicated, the measurement takes time, and it is impossible to deal with the examination in an emergency.

To solve the problems, Japanese Patent Application No. 2000-164990 discloses a method of employing a cellular component contraction agent so that cellular components in blood are contracted and develops on a chromatographic test strip. According to this method, the cellular component contraction agent is carried on the test strip so that a blood specimen is applied onto the chromatographic test strip without pretreatment. Although, in this method, the blood specimen can develop on the chromatographic specimen in a short time even without being somehow pretreated previously, a background value is increased and a S/N ratio is decreased due to influence of a blood pigment in the developing blood, whereby a sensitivity in a measurement employing a device is reduced, and the blood pigment prevents reading of a coloration degree, which results in extremely low accuracy for a quantitative measurement.

The present invention is made to solve the above-mentioned problems and has for its object to provide a biosensor which can simply and quickly analyze a measurement target in a liquid sample having a colored component without employing a particular device, and qualitatively or qualitatively analyze components to be measured more accurately.

SUMMARY OF THE INVENTION

According to one aspect of the present invention, there is provided a biosensor comprising a development layer where an inspection target solution is developed, and further comprising at least a marker reagent part where a marker reagent is held so as to be dissolved by the development of the inspection target solution in a part of the development layer, as well as a reagent immobilization part where a reagent which specifically reacts to an analysis target in the inspection target solution is immobilized in a part of the development layer, in which biosensor the development layer is provided with a bleaching reagent area where a reagent having bleaching action is carried in a dry state where it can be dissolved, at least in a part of a sample application area where the inspection target solution is applied or the downstream of the sample application area in the direction of the inspection target solution permeating.

According to the so-constituted biosensor, a colored component in the inspection target solution can be faded by the bleaching reagent, thereby visually judging the measurement result easily. Further, no blood pigment is attached onto the reactive layer, thereby extremely suppressing a reading error of the analysis target by a measuring device, resulting in a more accurate measurement result.

According to another aspect of the present invention and in the above-noted biosensor, the development layer is made of nitrocellulose.

According to the so-constituted biosensor, nitrocellulose which is a porous support body with minute spaces is employed, whereby an applying amount of the inspection target solution can be kept smaller.

According to another aspect of the present invention and in the above-noted biosensor, the reagent having bleaching action is directly carried on the development layer so as to be dissolved.

According to the so-constituted biosensor, there is no need to prepare a specific member where the reagent having bleaching action is previously carried, thereby reducing the number of members constituting the biosensor. Further, the inspection target solution is applied to the member where the bleaching reagent is directly carried, and thus the bleaching reagent develops without affecting permeability of the inspection target solution, thereby obtaining a highly sensitive and efficient measurement result due to more uniform bleaching action and reactivity.

According to yet another aspect of the present invention, a sample inflow area to which the inspection target solution flows in by a capillary phenomenon is arranged on the development layer, and the bleaching reagent area is held in the sample inflow area.

According to the so-constituted biosensor, the bleaching reagent is quickly dissolved with aspiration of the inspection target solution and a reaction is caused with the bleaching reagent, whereby a highly sensitive and efficient measurement result can be obtained due to more uniform bleaching action and reactivity.

According to still another aspect of the present invention, the inspection target solution to be applied is whole blood.

According to the so-constituted biosensor, the blood specimen is not required to be pretreated but is directly applied as a specimen, to be measured, whereby, in the case of measuring the analysis target in the blood, a simpler and quicker measurement is possible without requiring a conventionally employed large sized device, and a highly sensitive and efficient measurement result can be obtained.

According to one version of the present invention, the reagent having bleaching action is sodium percarbonate.

According to the so-constituted biosensor, negative effects on a protein or the like which is supposed to be important for the reaction can be suppressed extremely, thereby obtaining a highly sensitive and efficient measurement result.

According to an alternative version of the present invention, the reagent having bleaching action is hydrogen peroxide.

According to the so-constituted biosensor, bleaching can be performed in a shorter time and more efficiently, resulting in a simpler and quicker measurement as well as a highly sensitive and efficient measurement result.

According to yet another alternative version of the present invention, the reagent having bleaching action is sodium hypochlorite.

According to the so-constituted biosensor, negative effects on a protein or the like which is supposed to be important for the reaction can be suppressed extremely, thereby obtaining a highly sensitive and efficient measurement result.

According to another version of the present invention, the biosensor is a one-step immunochromatographic test strip.

According to the so-constituted biosensor, there is no necessity for pretreatment of the inspection target solution including cellular components, such as whole blood. Further, as an immunoreaction is utilized, a measurement target in wide fields can be measured by acquiring an antibody or an antigen for the measurement target, and a simple and quick measurement is possible when the inspection target solution including cellular components, such as the whole blood, is employed.

According to an alternative version of the present invention, the biosensor is a dry analysis element.

According to the so-constituted biosensor, the whole biosensor is a dry support body, and thus it is easy to carry and there is no need for strict management of preservation environment and condition, resulting in a biosensor which is easy to deal with, has no preference with respect to the preservation condition, and can be stored for a long time.

According to yet another aspect of the present invention, there is provided a biosensor comprising a development layer where an inspection target solution is developed, and further comprising at least a marker reagent part where a marker reagent is held so as to be dissolved by the development of the inspection target solution in a part of the development layer, as well as a reagent immobilization part where a reagent which specifically reacts to an analysis target in the inspection target solution is immobilized in a part of the development layer, in which biosensor the development layer is provided with areas where a cellular component contraction agent and a reagent having bleaching action are carried respectively so as to be dissolved, at least in parts of downstream of a sample application area where the inspection target solution is applied, in the direction of the inspection target solution permeating.

According to the so-constituted biosensor, when the inspection target solution including cellular components is applied, the cellular components gets contact with the cellular component contraction agent to be contracted, and thus the cellular components can permeate on the test strip efficiently and sufficiently even without adding a developing solution. That is, there is no necessity for pretreatment to previously remove the cellular components in the inspection target solution. Further, due to action of the bleaching reagent, a colored component in the liquid sample can be faded by the bleaching reagent, thereby visually judging a measurement result easily. Further, no blood pigment is attached onto the reactive layer, thereby extremely suppressing a reading error of the analysis target by a measuring device, resulting in a more accurate measurement result.

According to a version of the present invention, the development layer is made of nitrocellulose.

According to the so-constituted biosensor, nitrocellulose which is a porous support body with minute spaces is employed, whereby an applying amount of the inspection target solution can be kept smaller.

According to another version of the present invention, the reagent having bleaching action is directly carried on the development layer so as to be dissolved.

According to the so-constituted biosensor, there is no need to prepare a specific member where the reagent having bleaching action is previously carried, thereby reducing the number of members constituting the biosensor. Further, the inspection target solution is applied to the member where the bleaching reagent is directly carried, and thus the bleaching reagent develops without affecting permeability of the inspection target solution, thereby obtaining a highly sensitive and efficient measurement result due to more uniform bleaching action and reactivity.

According to yet another version of the present invention, a sample inflow area to which the inspection target solution flows in by a capillary phenomenon is arranged on the development layer, and the bleaching reagent area is held in the sample inflow area.

According to the so-constituted biosensor, immediately after the application, the inspection target solution dissolves the bleaching reagent quickly and causes a reaction with the bleaching reagent, whereby a highly sensitive and efficient measurement result can be obtained due to more uniform bleaching action and reactivity.

According to another version of the present invention, a mixed reagent of the cellular component contraction agent and the reagent having bleaching action is carried in the development layer.

According to the so-constituted biosensor, when the inspection target solution including cellular components is applied, the cellular components gets contact with the cellular component contraction agent to be contracted, and thus the cellular components can permeate on the test strip efficiently and sufficiently even without adding a developing solution. That is, there is no necessity for pretreatment to previously remove the cellular components in the inspection target solution. Further, due to action of the bleaching reagent, a colored component in the liquid sample can be faded by the bleaching reagent, thereby visually judging a measurement result easily. Further, no blood pigment is attached onto the reactive layer, thereby extremely suppressing a reading error of the analysis target by a measuring device, resulting in a more accurate measurement result. Further, the mixed cellular component contraction agent and bleaching reagent is carried, thereby reducing the number of members constituting the biosensor.

According to still another version of the present invention, a space is arranged on the development layer, through which the inspection target solution, getting contact therewith, flows in by a capillary phenomenon, and a mixed cellular component contraction agent and reagent having bleaching action are held in the space in a dry state where it can be dissolved by the inflow of the inspection target solution.

According to the so-constituted biosensor, there is arranged a space to which the inspection target solution flows in by a capillary reaction, and the mixed cellular component contraction agent and reagent with bleaching action is carried in the space, whereby the reagent can be dissolved quickly with aspiration of the inspection target solution.

According to still another version of the present invention, the inspection target solution to be applied is whole blood.

According to the so-constituted biosensor, the blood specimen is not required to be pretreated previously but directly applied as a specimen, to perform a measurement, whereby in the case of measuring the analysis target in the blood, a simpler and quicker measurement is possible without requiring a conventionally employed large sized device and a highly sensitive and efficient measurement result can be obtained.

According to still another version of the present invention, the reagent having bleaching action is sodium percarbonate.

According to the so-constituted biosensor, negative effects on a protein or the like which is supposed to be important for the reaction can be suppressed extremely, thereby obtaining a highly sensitive and efficient measurement result.

According to an alternative version of the present invention, the reagent having bleaching action is hydrogen peroxide.

According to the so-constituted biosensor, bleaching can be performed in a shorter time and more efficiently, resulting in a simpler and quicker measurement as well as a highly sensitive and efficient measurement result.

According to yet another alternative version of the present invention, the reagent having bleaching action is sodium hypochlorite.

According to the so-constituted biosensor, negative effects on a protein or the like which is supposed to be important for the reaction can be suppressed extremely, thereby obtaining a highly sensitive and efficient measurement result.

According to one version of the present invention, the cellular component contraction agent is inorganic salt.

According to the so-constituted biosensor, it is possible to analyze constituents of blood without inhibiting the reaction and perform a more accurate measurement in a short time.

According to another version of the biosensor of the present invention, the reagent having bleaching action is sodium percarbonate.

According to the so-constituted biosensor, it is possible to analyze constituents of blood without inhibiting the reaction and perform a more accurate measurement in a short time.

According to another version of the present invention, the cellular component contraction agent is a saccharide.

According to the so-constituted biosensor, it is possible to analyze constituents of blood without inhibiting the reaction and perform a more accurate measurement in a short time.

According to one version of the present invention, the biosensor is a one-step immunochromatographic test strip.

According to the so-constituted biosensor, there is no necessity for previous pretreatment of the inspection target solution including cellular components, such as whole blood. Further, as an immunoreaction is utilized, a measurement target in wide fields can be measured by acquiring an antibody or an antigen for the measurement target, and a simple and quick measurement is possible when the inspection target solution including cellular components, such as the whole blood, is employed.

According to an alternative version of the present invention, the biosensor is a dry analysis element.

According to the so-constituted biosensor, the whole biosensor is a dry support body, and thus it is easy to carry and there is no need for strict management of preservation environment and condition, resulting in a biosensor which is easy to deal with, has no preference with respect to the preservation condition, and can be stored for a long time.

DETAILED DESCRIPTION

Hereinafter, embodiments according to the present invention will be described with reference to the drawings. The embodiments described here are given only as examples and the present invention is not restricted to these embodiments.

Embodiment 1

A first embodiment of the present invention will be described with reference to FIG. 1.

Figure 1:
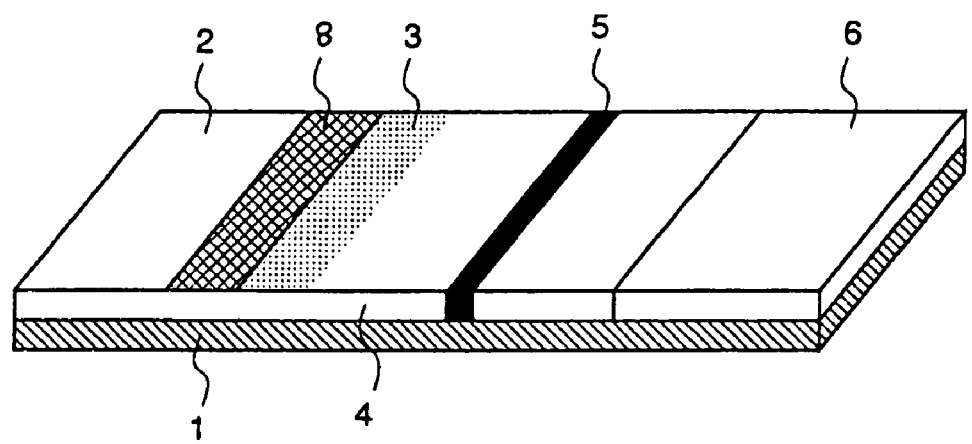
FIG. 1 is a perspective view illustrating the structure of a biosensor according to a first embodiment of the present invention.

FIG. 1 is a perspective view illustrating the structure of a biosensor according to the first embodiment of the present invention.

In FIG. 1, numeral 1 denotes a reactive layer carrier support body composed of a liquid-impermeable material such as a plastic, which supports chromatography materials. Numeral 2 denotes a sample application area composed of a nonwoven fabric or glass fiber filter paper having high absorptivity, or the like, to which an inspection target solution is added or applied, numeral 8 denotes a bleaching reagent hold region where a bleaching reagent having the action of a blood pigment is held so as to be dissolved, numeral 3 denotes a marker hold region where a marker reagent is held so as to be dissolved, numeral 4 denotes a reactive layer made of nitrocellulose or the like, in which the sample is developed to cause a reaction, numeral 5 denotes a specific protein immobilization part in which a specific protein is immobilized on the region of the reactive layer 4, and numeral 6 denotes a water absorbing area which absorbs the inspection target solution finally. The respective regions of the sample application area 2, the marker hold region 3, the reactive layer 4, the specific protein immobilization part 5, the water absorbing area 6, and the bleaching reagent hold region 8 are formed being laminated or connected on the reactive layer carrier support body 1.

An operation of the so-constituted biosensor will be described with reference to FIG. 1.

First, when a whole blood specimen is applied to the sample application area 2 as an inspection target solution, the whole blood specimen reaches the area of the bleaching reagent hold region 8. Then, a bleaching reagent held in the area of the bleaching reagent hold region 8 is dissolved due to permeation of the whole blood specimen, and the whole blood specimen reaches the area of the marker hold region 3 while the color of constituents of blood fading. Next, a marker reagent held in the area of the marker hold region 3 is dissolved due to the permeation of the whole blood specimen and permeates into the region of the reactive layer 4. On the region of the reactive layer 4, there is the specific protein immobilization part 5 in which a specific protein is immobilized, and a reaction is caused between the marker reagent eluted from the area of the marker hold region 3 as well as an analysis target in the whole blood specimen and the specific protein. At this time, when the analysis target exists in the whole blood specimen, some color reaction is seen in the region of the specific protein immobilization part 5. The whole blood specimen is finally absorbed into the water absorbing area 6, and the reaction is ended.

As described above, the biosensor according to the first embodiment includes the bleaching reagent having bleaching action on the reactive layer carrier support body, a component pigment in the inspection target solution fades with the elution of the bleaching reagent, and coloring on the reactive layer except for a judgement region can be suppressed, thereby visually judging a measurement result easily. Further, also in a measurement employing a measuring device, influence of a background due to a blood pigment can be kept extremely low. Further, it is not required to previously separate cellular components such as blood corpuscles and there is no influence of the blood pigment, resulting in a simple, quick, and high-accuracy qualitatively or quantitatively analysis.

While in this first embodiment the sample application area 2 and the bleaching reagent hold region 8 are constituted individually, it is also possible that the sample application area 2 is eliminated and the bleaching reagent hold region 8 also serves as the sample application area 2. According to this structure, the number of members constituting the biosensor can be reduced. Further, since the inspection target solution is applied to the member where the bleaching reagent is carried directly, the bleaching reagent can develop without being affected by permeability of the inspection target solution, thereby obtaining a highly sensitive and efficient measurement result due to more uniform bleaching action and reactivity.

While the description has been given of a case where the structure in FIG. 1 is made of the plural members, it is also possible that the bleaching reagent hold region 8 and the marker reagent hold region 3 where the bleaching reagent and the marker reagent are held on the reactive layer 4 made of a porous support body such as nitrocellulose so as to be dissolved, respectively, and the specific protein immobilization part 5 where a specific protein is immobilized, are formed on the same support body.

Embodiment 2

Hereinafter, a second embodiment of the present invention will be described with reference to FIGS. 2 and 3.

Figure 2:
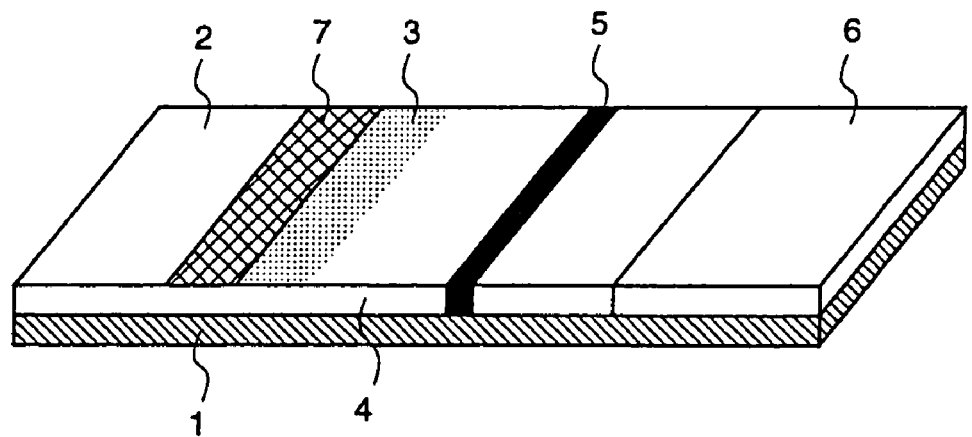
FIG. 2 is a perspective view illustrating the structure of a biosensor according to a second embodiment of the present invention.
Figure 3:
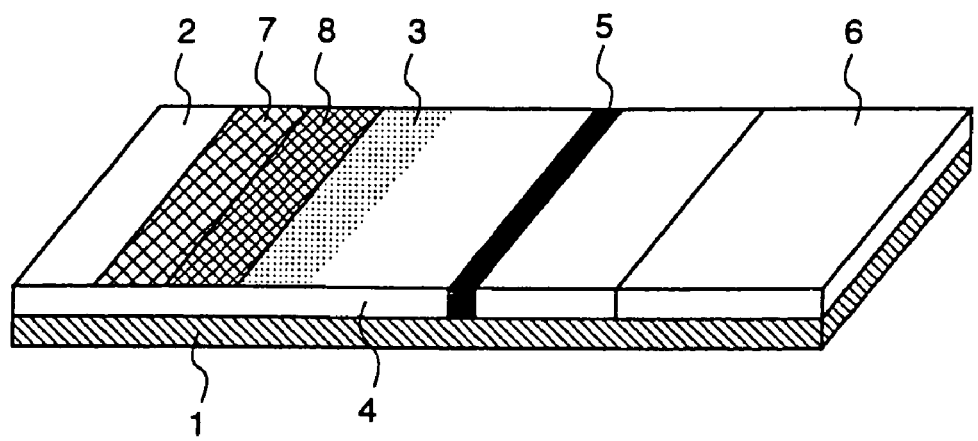
FIG. 3 is a perspective view illustrating the structure of another biosensor according to the second embodiment of the invention.

FIG. 2 is a perspective view illustrating the structure of a biosensor according to the second embodiment of the present invention, and FIG. 3 is a perspective view illustrating the structure of another biosensor according to the second embodiment of the present invention.

In FIGS. 2 and 3, numeral 7 denotes a contraction agent hold region where a cellular component contraction agent is held so as to be dissolved. With respect to other constitutions, the same regions as those shown in FIG. 1 will be denoted by the same reference numerals and their descriptions will be omitted. The respective regions of the sample application area 2, the marker hold region 3, the reactive layer 4, the specific protein immobilization part 5, the water absorbing area 6, the contraction agent hold region 7, and the bleaching reagent hold region 8 are formed being laminated or connected on the reactive layer carrier support body 1.

Here, the cellular component contraction agent is one which employs inorganic salt, an amino acid or a saccharide. The inorganic salt indicates an inorganic compound including salt, such as sodium chloride, potassium chloride and sodium phosphate, the amino acid indicates a compound having a carboxyl group and an amino group in the identical molecule, such as a glycin and a glutamic acid, and the amino acid also includes an imino acid such as a proline and a hydroxylproline, and the saccharide indicates a glucide such as a glucose, a sucrose and a trehalose, or sugar alcohol such as glucitol.

An operation of the so-constituted biosensor will be described with reference to FIG. 2.

First, when a whole blood specimen as an inspection target solution is applied to the sample application part 2, the whole blood specimen reaches the area of the contraction agent hold region 7. Then, the whole blood specimen reaches the area of the marker hold region 3 while cellular components being contracted with elution of the cellular component contraction agent. Next, a marker reagent held in the area of the marker hold region 3 is dissolved due to permeation of the whole blood specimen and permeates into the region of the reactive layer 4. On the region of the reactive layer 4, there is the specific protein immobilization part 5 in which a specific protein is immobilized, and a reaction is caused between the marker reagent eluted from the area of the marker hold region 3 as well as an analysis target in the whole blood specimen and the specific protein. At this time, when the analysis target exists in the whole blood specimen, some color reaction is seen in the region of the specific protein immobilization part 5. The whole blood specimen is finally absorbed into the water absorbing area 6, and the reaction is ended.

Next, an operation of the above-mentioned biosensor with another structure will be described with reference to FIG. 3.

First, when a whole blood specimen as an inspection target solution is applied to the sample application part 2, the whole blood specimen reaches the area of the contraction agent hold region 7. Then, the whole blood specimen reaches the area of the bleaching reagent hold region 8 while cellular components being contracted with elution of the cellular component contraction agent. A bleaching reagent held in the area of the bleaching reagent hold region 8 is dissolved due to permeation of the whole blood specimen, and the whole blood specimen reaches the area of the marker hold region 3 while a pigment of constituents of blood fading. Next, a marker reagent held in the area of the marker hold region 3 is dissolved due to the permeation of the whole blood specimen and permeates into the region of the reactive layer 4. On the region of the reactive layer 4, there is the specific protein immobilization part 5 in which a specific protein is immobilized, and a reaction is caused between the marker reagent eluted from the area of the marker hold region 3 as well as an analysis target in the whole blood specimen and the specific protein. At this time, when the analysis target exists in the whole blood specimen, some color reaction is seen in the region of the specific protein immobilization part 5. The whole blood specimen is finally absorbed into the water absorbing area 6, and the reaction is ended.

The cellular component contraction agent shown here employs the property of membrane equilibrium possessed by a cell to contract the cell by the action of osmotic pressure under a state where substance through which the cell can pass is in a concentrated form. Further, it is desirable that the cellular component contraction agent is a substance with the effect of contracting the cell by the action of osmotic pressure.

As described above, the biosensor according to the second embodiment includes the contraction agent hold region where the cellular component contraction agent is held on the reactive layer carrier support body, whereby contracted cellular components can permeate even on a porous support body with small size pores, such as nitrocellulose, without clogging, and the whole blood specimen can be used without being somehow pretreated previously.

Further, the bleaching reagent hold region where the bleaching reagent having bleaching action is held is further provided on the downstream side of the contraction agent hold region, toward which the liquid sample permeates, whereby a pigment of constituents of blood in the liquid sample fades with the elution of the bleaching reagent, so that coloring of the blood pigment permeating on the reactive layer support body can be kept low, and therefore a color reaction after the development of the liquid sample can be visually confirmed easily and influence of a background due to the blood pigment can be kept extremely low also in a measurement employing a measuring device.

While in this second embodiment the sample application area 2 and the bleaching reagent hold region 8 are constituted individually, it is also possible that the sample application area 2 is eliminated and the bleaching reagent hold region 8 also serves as the sample application area 2. According to this structure, the number of members constituting the biosensor can be reduced. Further, since the inspection target solution is applied to the member where the bleaching reagent is carried directly, the bleaching reagent can develop without being affected by permeability of the inspection target solution, thereby obtaining a highly sensitive and efficient measurement result due to more uniform bleaching action and reactivity.

While the description has been given of a case where the structures in FIGS. 2 and 3 are made of the plural members, it is also possible that the contraction agent hold area 7, the bleaching reagent hold region 8 and the marker reagent hold region 3 where the cellular component contraction agent, the bleaching reagent and the marker reagent are held on the reactive layer 4 made of a porous support body such as nitrocellulose so as to be dissolved, respectively, and the specific protein immobilization part 5 where a specific protein is immobilized, are formed on the same support body.

Embodiment 3

Hereinafter, a third embodiment of the present invention will be described with reference to FIGS. 4 and 5.

Figure 4:
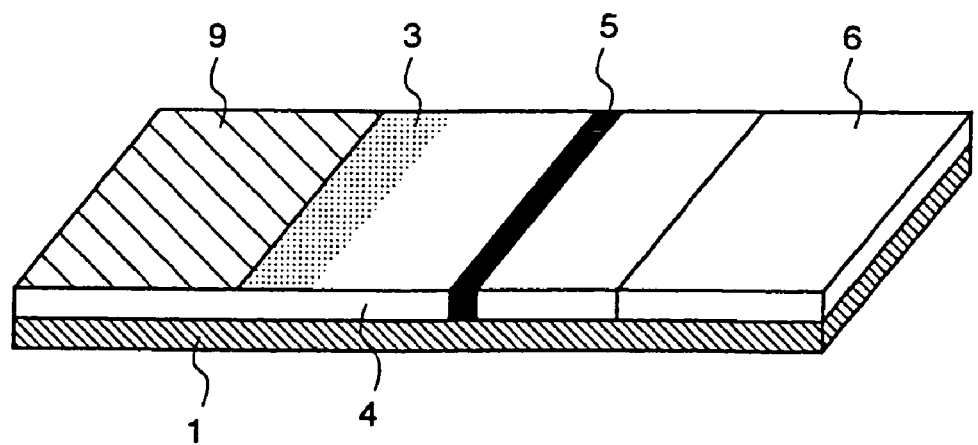
FIG. 4 is a perspective view illustrating the structure of a biosensor according to a third embodiment of the present invention.
Figure 5:
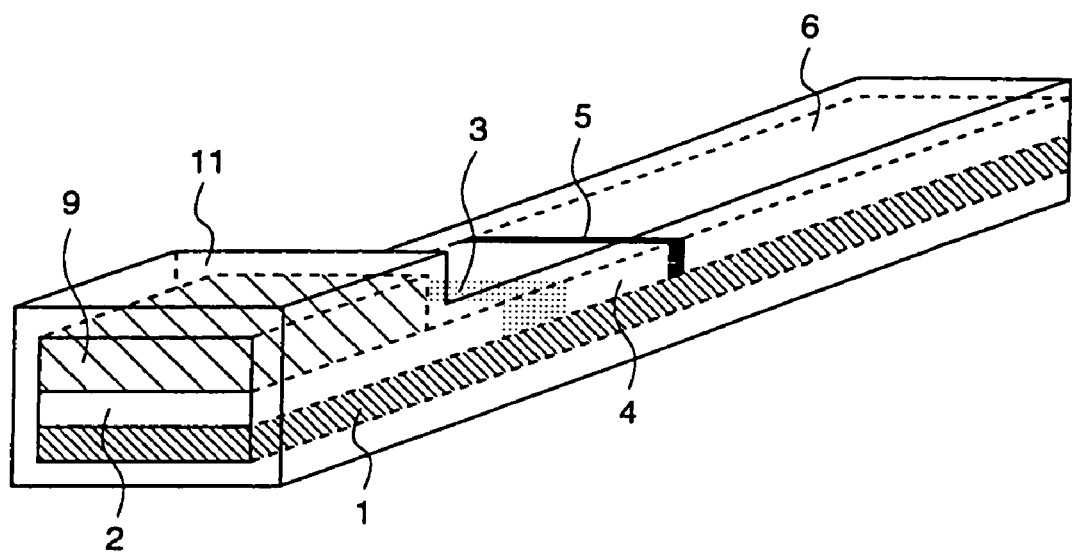
FIG. 5 is a perspective view illustrating the structure of another biosensor according to the third embodiment of the invention.

FIG. 4 is a perspective view illustrating the structure of a biosensor according to the third embodiment of the present invention, and FIG. 5 is a perspective view illustrating the structure of another biosensor according to the third embodiment of the present invention.

In FIG. 4, numeral 9 denotes a mixed reagent hold region where a mixed reagent of a cellular component contraction agent and a bleaching reagent is held so as to be dissolved. With respect to other constitutions, the same parts as those shown in FIG. 1 will be denoted by the same reference numerals and their descriptions will be omitted. The respective regions of the marker hold region 3, the reactive layer 4, the specific protein immobilization part 5, the water absorbing area 6, and the mixed reagent hold region 9 are formed on the reactive layer carrier support body 1.

In FIG. 5, numeral 11 denotes a sample inflow area which is provided on the sample application area 2 and forms a space area so that an inspection target solution can flow therein by a capillary phenomenon. With respect to other constitutions, the same parts as those shown in FIG. 1 will be denoted by the same reference numerals and their descriptions will be omitted. The respective regions of the sample application area 2, the marker hold region 3, the specific protein immobilization part 3, and the water absorbing area 6 are formed on the reactive layer carrier support body 1. The mixed reagent hold region 9 is formed on the sample application area 2.

Next, an operation of the so-constituted biosensors will be described with reference to FIGS. 4 and 5.

First, when an inspection target solution is applied or aspirated, the liquid sample reaches the area of the marker hold region 3 while cellular components being contracted with elution of the mixed reagent and a colored component fading in the mixed reagent hold region 9. Then, a marker reagent held in the area of the marker hold region 3 is dissolved due to the permeation of the liquid sample and permeates into the region of the reactive layer 4. On the region of the reactive layer 4, there is the specific protein immobilization part 5 in which a specific protein is immobilized, and a reaction is caused between the marker reagent eluted from the area of the marker hold region 3 as well as an analysis target in the inspection target solution and the specific protein. At this time, when the analysis target exists in the inspection target solution, some color reaction is seen in the region of the specific protein immobilization part 5. The inspection target solution is finally absorbed into the water absorbing area 6, and the reaction is ended.

As described above, according to the biosensor of the third embodiment, the mixed reagent hold region for the mixed reagent of the cellular component contraction agent and the bleaching reagent is held on the reactive layer 4 on the reactive layer carrier support body, whereby the cellular components in the inspection target solution are contracted with the elution of the cellular component contraction agent and the contracted cellular components permeate even on the porous support body with small size pores, such as nitrocellulose, without clogging, and the inspection target solution including the cellular components, such as whole blood specimen, can be used without being somehow pretreated previously. Further, the bleaching reagent having bleaching action is also mixed in the mixed reagent, whereby a component of a pigment, such as a pigment of constituents of blood, in the inspection target solution, fades with the elution of the bleaching reagent. Therefore, coloring of the blood pigment permeating on the reactive layer support body can be kept low, whereby a color reaction after the development of the liquid sample can be visually confirmed easily and, also in a measurement employing a measuring device, influence of a background due to the blood pigment can be kept extremely low.

Further, the space forming part where a space area is formed so that the inspection target solution can flow therein by a capillary phenomenon is provided, whereby the mixed reagent, which is held in the space forming part, is dissolved with the aspiration of the inspection target solution, so that the cellular components are contracted and the pigment component fades. Therefore, the permeation can occur even on the porous support body with small size pores, such as nitrocellulose, without clogging and thus the inspection target solution including the cellular components, such as the whole blood specimen, can be used without being somehow pretreated previously, and further coloring of a pigment of the blood permeating on the reactive layer support body can be kept low and thus a color reaction after the development of the liquid sample can be visually confirmed easily. Further, also in a measurement employing a measuring device, influence of a background due to the blood pigment can be kept extremely low.

While in this third embodiment the liquid sample is directly applied to the mixed reagent hold region 9 in FIG. 4, the sample application area 2 may be provided on the upstream side of the mixed reagent hold region in the direction of the inspection target solution permeating. Further, while the mixed reagent is held in the space on the sample application area 2 in FIG. 5, it is also possible that either one of the cellular component contraction agent and the marker reagent is provided on the reactive layer and the other is held in the space.

The structures in FIGS. 4 and 5 may be either the structure in which the marker reagent hold region 3 and the water absorbing area 6 are made of plural different members or the structure in which the marker reagent hold region 3 is held on the reactive layer 4 and a single layer member without the water absorbing area is formed on the support body.

Embodiment 4

Hereinafter, a fourth embodiment of the present invention will be described with reference to FIGS. 6 to 14.

Figure 6:
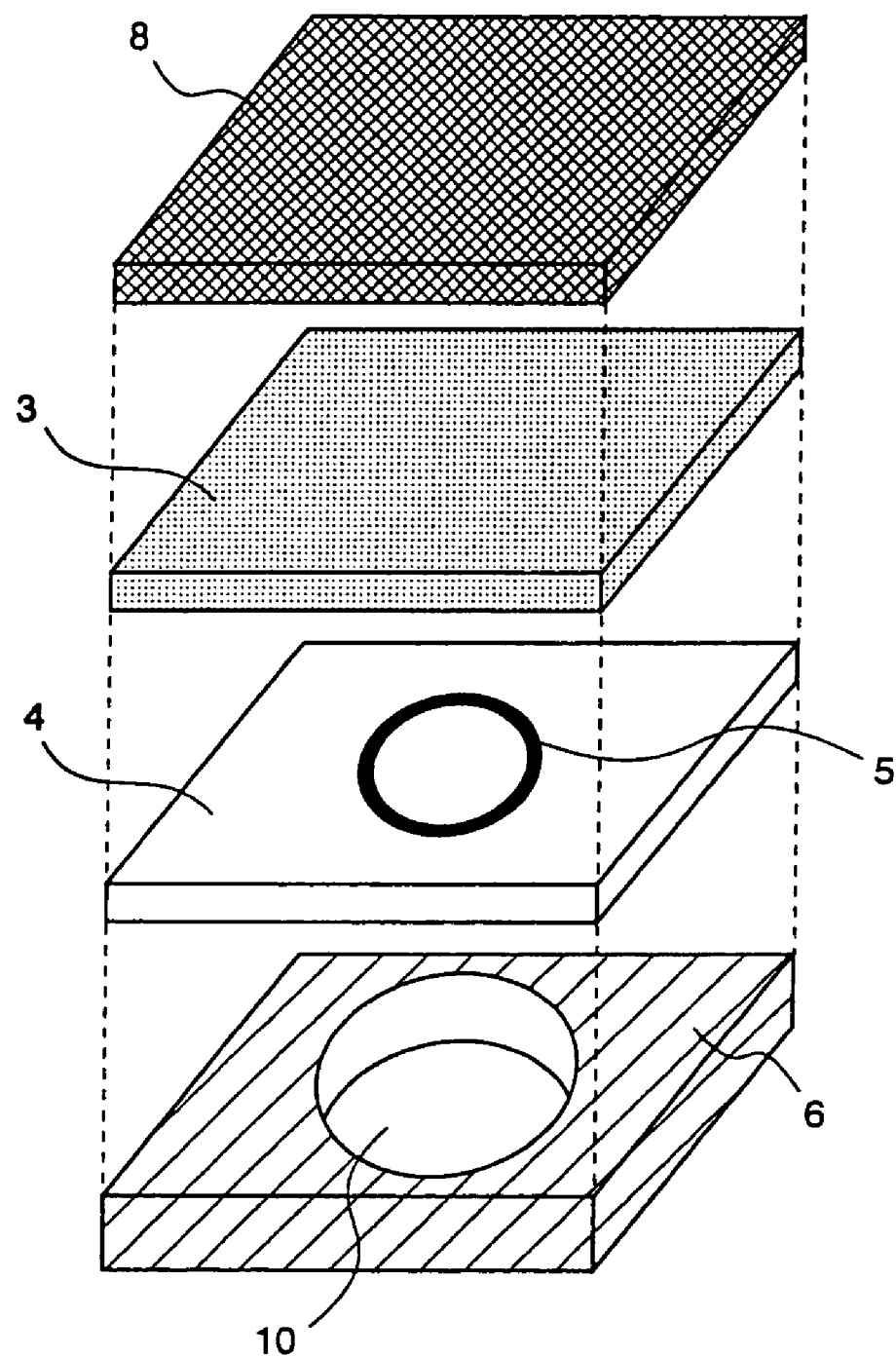
FIG. 6 is a perspective view illustrating the structure of a biosensor according to a fourth embodiment of the present invention.

FIG. 6 is a perspective view illustrating the structure of a biosensor according to the fourth embodiment of the present invention.

In FIG. 6, numeral 10 denotes a result confirmation window for confirming a result on the reactive layer 4. With respect to other constitutions, the same parts as those shown in FIG. 1 will be denoted by the same reference numerals and their descriptions will be omitted. The respective regions are formed being laminated in order of the water absorbing area 6, the reactive layer 4, the marker hold region 3 and the bleaching reagent hold region 8 to form a test strip.

Figure 7:
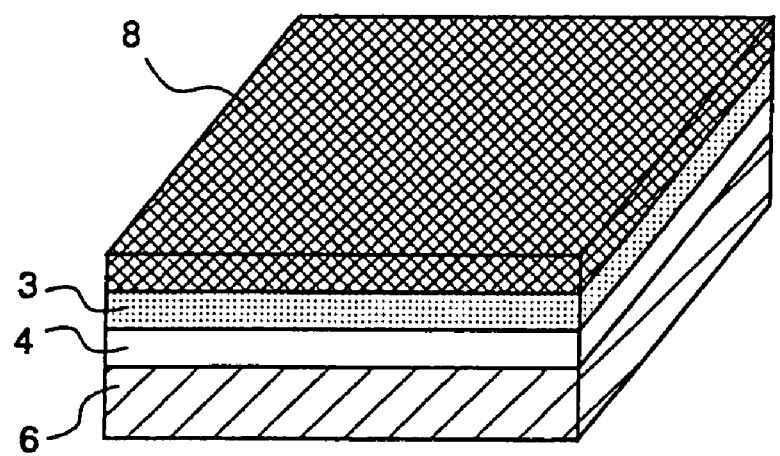
FIG. 7 is a perspective view of FIG. 6 from the viewpoint of a bleaching reagent hold region.
Figure 8:
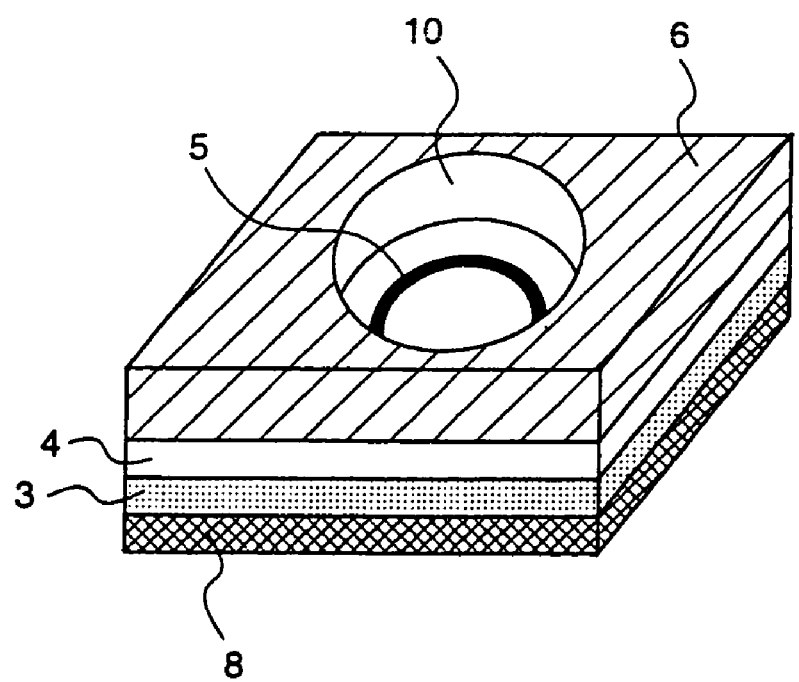
FIG. 8 is a perspective view of FIG. 6 from the viewpoint of a water absorbing area.
Figure 9:
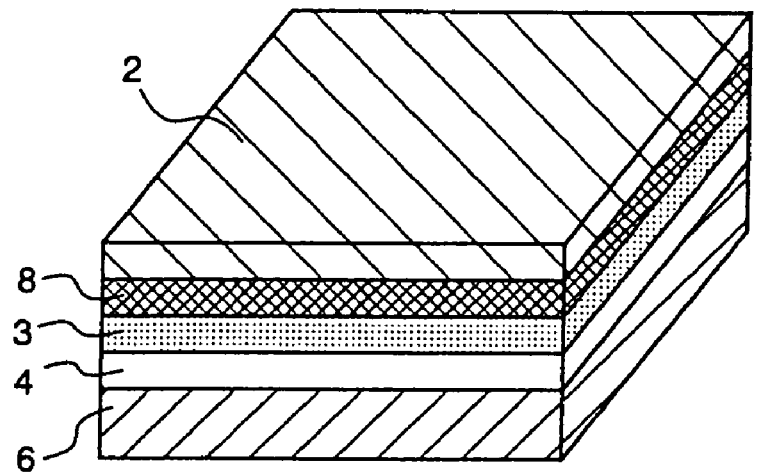
FIG. 9 is a perspective view of a structure in which a sample application area is held on the bleaching reagent hold region in FIG. 7.
Figure 10:
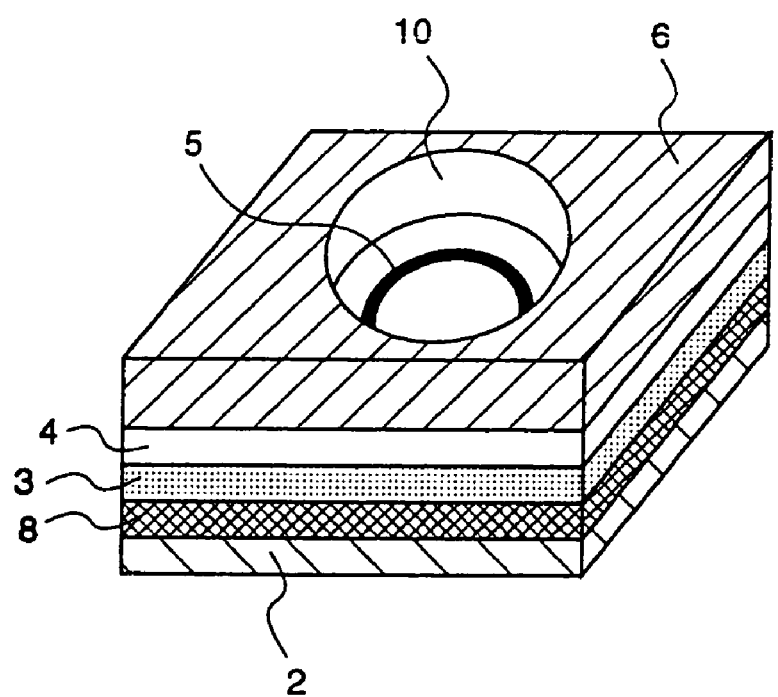
FIG. 10 is a perspective view of a structure in which the sample application area is held under the bleaching reagent hold region in FIG. 8.

FIG. 7 is a perspective view of the test strip shown in FIG. 6 from the viewpoint of the bleaching reagent hold region 8, and FIG. 8 is a perspective view of the test strip shown in FIG. 6 from the viewpoint of the water absorbing area 6. FIG. 9 is a perspective view of a test strip from the viewpoint of the sample application part, in which test strip the sample application area 2 to which an inspection target solution is added or applied, which is composed of a nonwoven fabric or glass fiber filter paper having a high absorptivity, is laminated on the bleaching reagent hold region 8 shown in FIG. 6, and FIG. 10 is a perspective view of FIG. 9 from the viewpoint of the water absorbing area 6.

Figure 11:
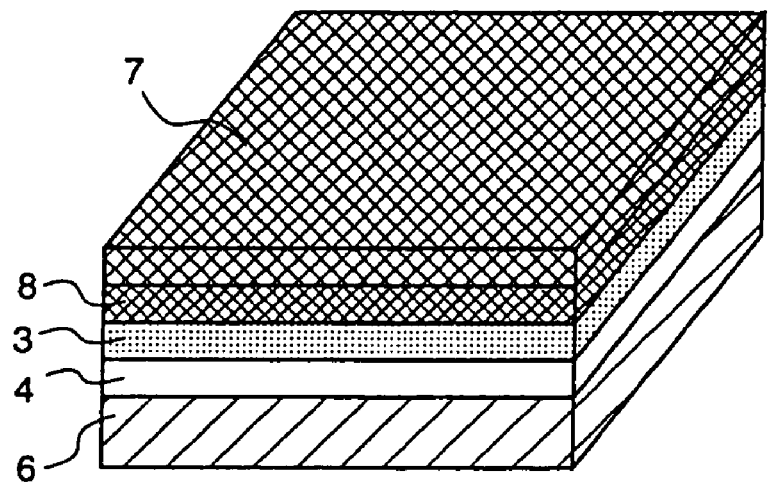
FIG. 11 is a perspective view of a structure in which a contraction agent hold region is held on the bleaching reagent hold region in FIG. 7.
Figure 12:
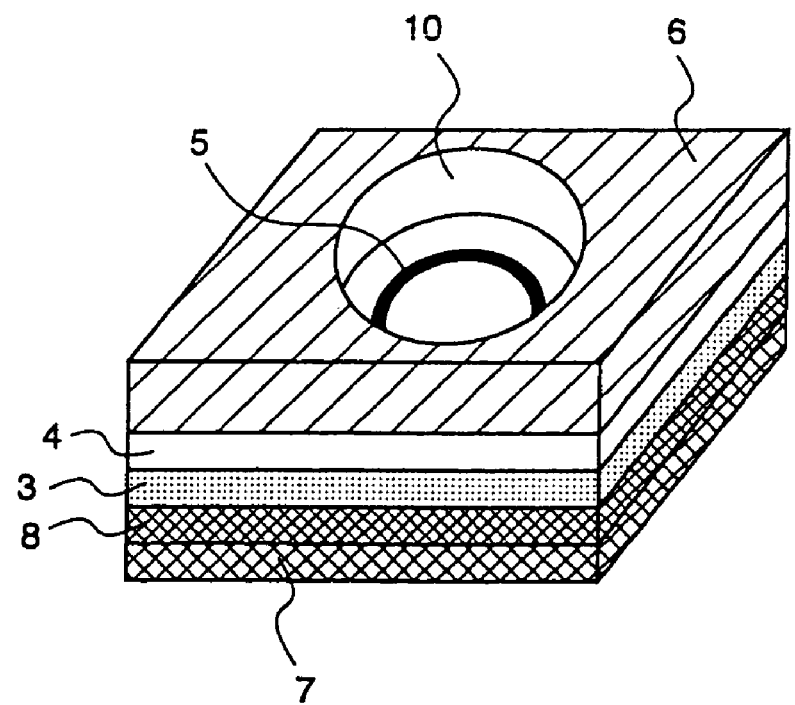
FIG. 12 is a perspective view of a structure in which the contraction agent hold region is held under the bleaching reagent hold region in FIG. 8.

FIG. 11 is a perspective view of a test strip from the viewpoint of the cellular component contraction agent hold region 7, in which the cellular component contraction agent hold region 7 where the cellular component contraction agent is held in a nonwoven fabric, glass fiber filter paper or the like so as to be dissolved is laminated on the bleaching reagent hold region 8 shown in FIG. 6, and FIG. 12 is a perspective view of FIG. 11 from the viewpoint of the water absorbing area 6.

Figure 13:
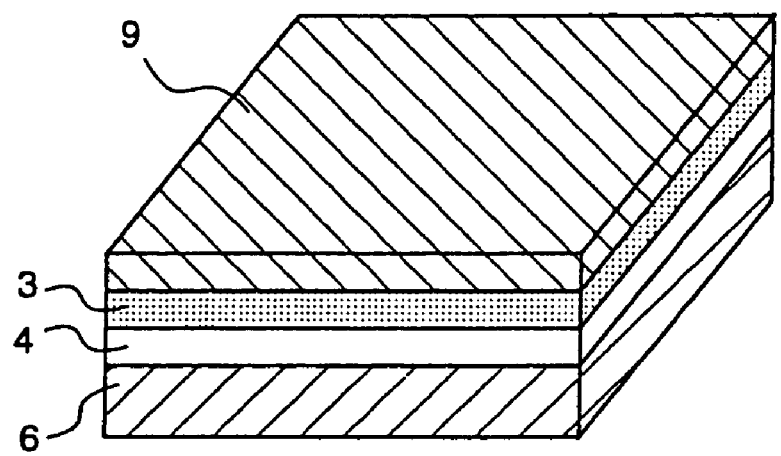
FIG. 13 is a perspective view of a structure in which the bleaching reagent hold region in FIG. 7 is changed to a mixed reagent hold region.
Figure 14:
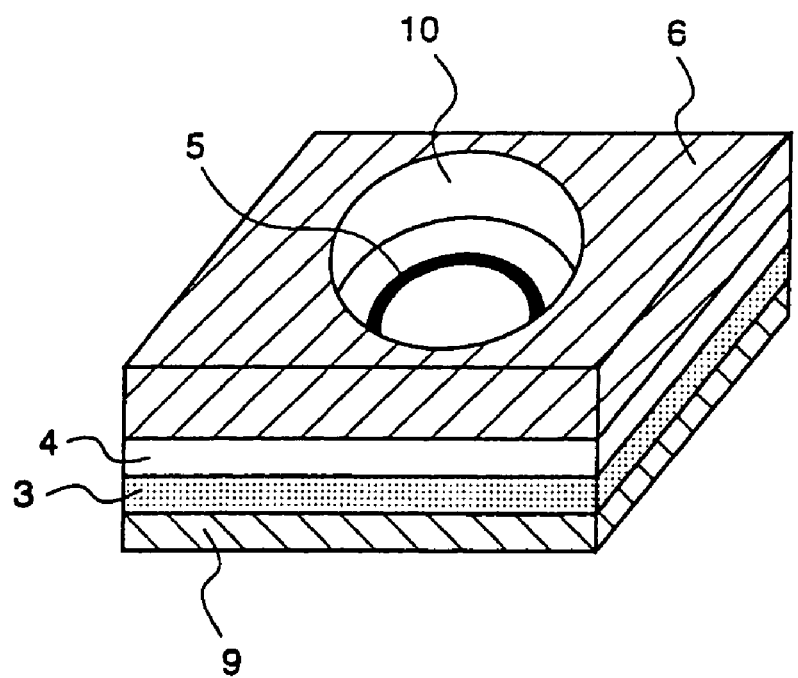
FIG. 14 is a perspective view of a structure in which the bleaching reagent hold region in FIG. 8 is changed to a mixed reagent hold region.

FIG. 13 is a perspective view of a test strip from the viewpoint of the mixed reagent hold region 9, in which the mixed reagent hold region 9 for the mixed reagent of the cellular component contraction agent and the bleaching reagent, which is changed from the bleaching reagent hold region 8 shown in FIG. 6, is laminated, and FIG. 14 is a perspective view of FIG. 13 from the viewpoint of the water absorbing area 6.

Next, an operation of the so-constituted biosensor will be described with reference to FIGS. 6 to 14.

First, when an inspection target solution is applied to the sample application part 2, it reaches the area of the contraction agent hold region 7. The inspection target solution reaches the area of the bleaching reagent hold region 8 while cellular components being contracted with elution of the contraction agent. A bleaching reagent held in the area of the bleaching reagent hold region 8 is dissolved due to permeation of the inspection target solution, and reaches the area of the marker hold region 3 while a pigment component such as a blood pigment fading. A marker reagent held in the area of the marker hold region 3 is dissolved due to the permeation of the inspection target solution and permeates into the region of the reactive layer 4. On the region of the reactive layer 4, there is the specific protein immobilization part 5 in which a specific protein is immobilized, and a reaction is caused between the marker reagent eluted from the area of the marker hold region 3 as well as an analysis target in the inspection target solution and the specific protein. At this time, when the analysis target exists in the inspection target solution, some color reaction is seen in the region of the specific protein immobilization part 5. The inspection target solution is finally absorbed into the water absorbing area 6, and the reaction is ended. Then, the result of the measurement is confirmed visually through the result confirmation window 10.

As described above, according to the biosensor of the fourth embodiment, the area where the cellular component contraction agent is held is constituted on the test strip, whereby no clogging occurs due to the cellular components and the liquid component in the inspection target solution can permeate into the reactive layer 4 quickly, and even when the inspection target solution including the cellular components such as a specimen is applied, the inspection target solution does not require a previous pretreatment but is directly applied, to perform a measurement. Further, since the bleaching reagent hold region is constituted on the test strip, the pigment component in the inspection target solution fades with the elution of the marker reagent, and coloring on the reactive layer except for a judgement region can be suppressed, thereby performing a qualitative or quantitative measurement more simply, quickly and highly efficiently without being affected by a blood pigment.

As described above, according to the biosensors of the first to fourth embodiments, a test strip which is made of a chromatography material composed of an arbitrary porous support body such as nitrocellulose, a nonwoven fabric and glass fiber filter paper is employed, whereby it is possible to analyze, detect, and qualitatively or quantitatively measure specific substance employing an arbitrary measurement principle such as an antigen antibody reaction.

While in the first to fourth embodiments the descriptions have been given taking the antigen antibody reaction employing a marker as an example, any markers which produce some change before and after the reaction, such as an enzyme, are available.

Further, according to the biosensors of the first to fourth embodiments, the inspection target solution applied to the test strip is whole blood, and thus the blood specimen is not previously pretreated but is directly applied as a specimen, to perform a measurement, whereby a conventionally employed large sized device is not required when measuring the analysis target in the blood, resulting in a simpler and quicker measurement and a highly sensitive and efficient measurement result.

Further, according to the biosensors of the first to fourth embodiments, the marker reagent may be a metallic sol, a nonmetallic sol, a dye sol, coloring particles, coloring matters, an enzyme, a protein and the like, and any of these markers can be employed.

By this constitution, no pretreatment is required previously even when the inspection target solution including the cellular components, such as the blood specimen, is measured, and there is no influence of the pigment component, thereby performing a simpler, quicker and highly sensitive and efficient measurement.

Further, according to the biosensors of the first to fourth embodiments, a one-step immunochromatographic test strip is also available. By this constitution, the inspection target solution including the cellular components, such as whole blood, is not required to be pretreated previously, a measurement target in wide fields can be measured by acquiring an antibody or an antigen for the measurement target utilizing an immunoreaction, and a simple and quick measurement is possible even when the inspection target solution including cellular components, such as the whole blood, is employed. "One-step" mentioned here indicates an operation which only requires the application of the inspection target solution to the test strip, without requiring a pretreatment of the inspection target solution including the cellular components, such as the whole blood, employing a developing solution which is different from the inspection target solution on the test strip before and after the application of the inspection target solution, and requiring an operation of washing a chromatographic support body which aims at B/F separation, in its measuring operation, and "immunochromatographic test strip" indicates a sensor for detecting inspection target substance in the inspection target solution utilizing the antigen antibody reaction on a support body where chromatographic development is performed.

Further, according to the biosensors of the first to fourth embodiments, an immunochromatographic test strip of a dry analysis element is also available. By this constitution the whole biosensor is a dry support body, and thus it is easy to carry and there is no necessity for strict preservation environment and condition, resulting in a biosensor which is easy to deal with, has no preference with respect to the preservation condition, and can be stored for a long time. Further, "dry analysis element" mentioned here indicates one in which all the members constituting the biosensor as well as the carried reagent are in a dry state.

EXAMPLE

A method for implementing the present invention will be described in more detail through the following example. The present invention is not restricted by the following example.

Example 1

Quantitative measurement of hCG in whole blood by lateral flow-type chromatographic sensor.

a) Preparation of Chromatography Test Strip

First, an anti-hCG-β antibody solution which was diluted with a phosphate buffer solution to control the concentration was prepared. This antibody solution was applied on the nitrocellulose film by employing a solution discharge device. Thereby, a detecting antibody immobilization line was obtained on the nitrocellulose film. After being dried, this nitrocellulose film was immersed in a Tris-HCl buffer solution including 1% skim milk and shaken gently for 30 minutes. 30 minutes later, the film was moved into a Tris-HCl buffer solution tank, shaken gently for 10 minutes, and thereafter shaken gently in another Tris-HCl buffer solution tank for another 10 minutes, to wash the film. After washed twice, the film was taken out from the solution tank, and dried at room temperature.

Preparation of the gold colloid was performed by adding 1% citric acid solution to a refluxing 100° C.-solution of 0.01% chloroauric acid. After the reflux was continued for 30 minutes, it was cooled left at room temperature. The anti-hCG-α antibody was added to gold colloid solution which was prepared to pH9 by using 0.2M potassium carbonate solution, then the obtained solution was stirred for several minutes, and then 10% BSA (bovine serum albumin) solution of pH9 was added thereto by such an amount that 1% solution was finally obtained and stirred. Thereby, an antibody-gold colloid complex (marker antibody) was prepared. The marker antibody solution was centrifuged at 4° C. and 20000 G for 50 minutes, whereby the marker antibody was isolated, and the isolated marker antibody was suspended in a washing buffer solution (1% BSA⎵phosphate buffer solution) and thereafter centrifuged to wash and isolate the marker antibody. After suspended in the washing buffer solution and filtrated through a 0.8 μm filter, the marker antibody was prepared to one-tenth as much as the initial gold colloid solution and stored at 4° C.

The marker antibody solution was set in the solution discharge device and applied to a position on an anti-hCG-β antibody immobilization dry film, apart from an antibody immobilization position, and thereafter the film was dried. Thereby, the marker antibody hold region was obtained on the immobilization film.

0.1 ml of mixed water solution of potassium chloride prepared to 0.15M and sodium percarbonate prepared to 0.05% was applied to a nonwoven fabric per unit area, immediately frozen by liquid nitrogen, and freeze-dried. Therefore, the mixed reagent hold member permeated by the potassium chloride and the sodium percarbonate was obtained. Further, the hold member for only the potassium chloride, which is the cellular component contraction agent not including the 0.05% sodium percarbonate, was also manufactured similarly.

The antibody immobilization film including the marker antibody hold region prepared as described above was affixed on the reactive layer carrier support, the mixed reagent hold member or the cellular component contraction agent hold member was added thereto, glass fiber filter paper was added thereto as the water absorbing area, and thereafter the film was cut into small pieces of 0.5 cm width, thereby manufacturing the test strip.

b) Preparation of Sample

Human blood to which heparin was added as an anticoagulant was prepared to have a hematocrit value of 45%. The hCG solutions of known concentrations were added to this blood, thereby preparing the hCG solutions of various known concentrations.

c) Measurement of the Degree of Coloration on Test Strip

More than 200 μl of blood including hCG was applied to the sample application part on the test strip and developed in the direction of the water absorbing area, to cause an antigen-antibody reaction, whereby a color reaction in the antibody immobilization part was caused. The coloration state 5 minutes after the sample application to this test strip was measured by employing a reflective spectrophotometer (CS9300; Shimadzu Corporation made), and the coloration degree was computed.

Bloods (hematocrit values of 45%) including hCG of 0, 100, 1000, and 10000 U/l were applied to the test strip to be developed. The coloration state of the antibody immobilization part on the test strip for blood of each hCG concentration was measured by the reflective spectrophotometer. An absorbance at the wavelength of 635 nm was measured, and substituted into a previously formed calibration curve indicating a relationship between the hCG concentration and the absorbance. The result is shown in FIG. 15.

Figure 15A:
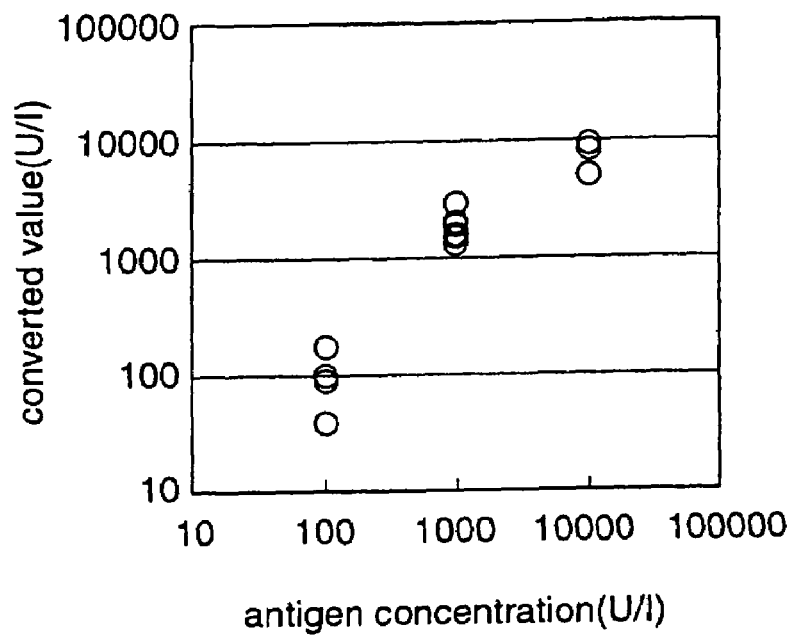
FIG. 15 are diagrams showing an efficiency difference in a coloration degree measurement between in a case where a reagent having bleaching action is held in a test strip and in a case where the reagent is not held.
Figure 15B:
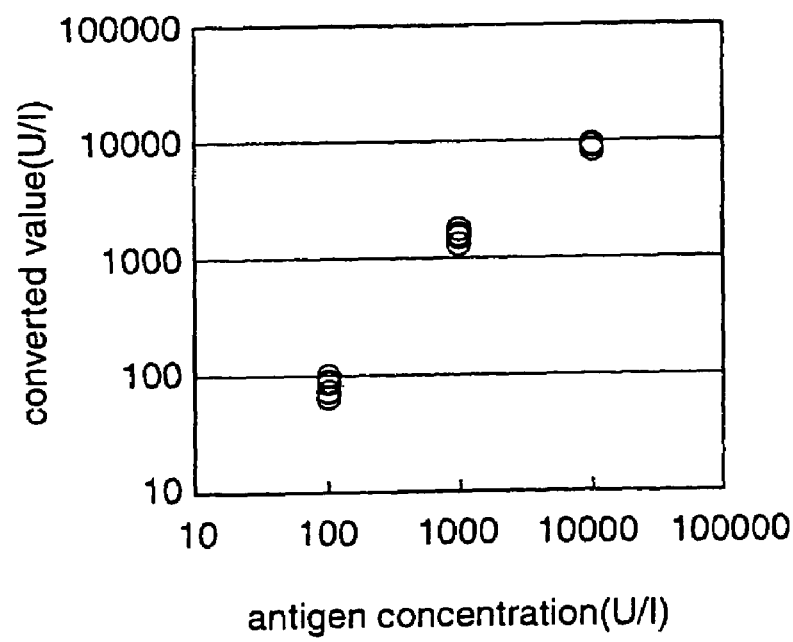
Figure 16:
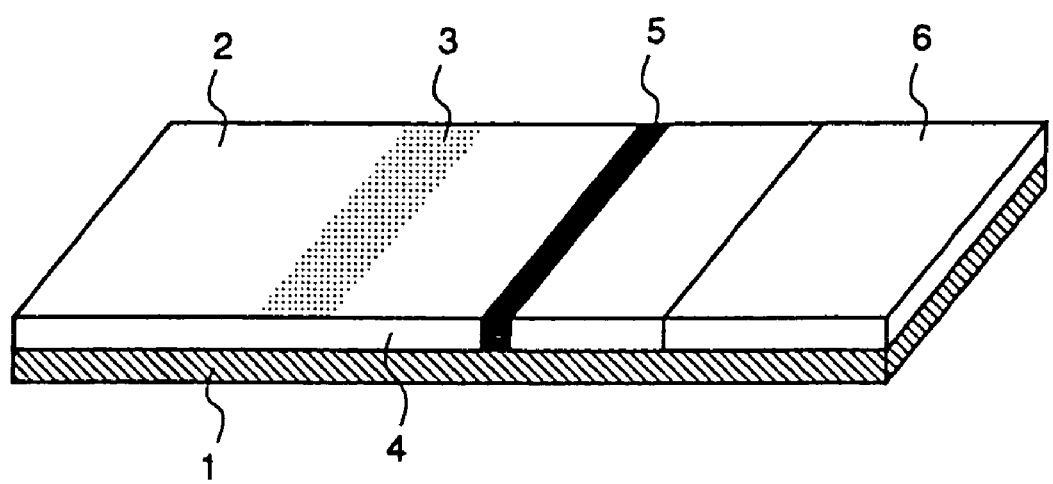
FIG. 16 is a perspective view illustrating the structure of a conventional biosensor.

FIG. 15 are diagrams illustrating efficiencies in measurement of the coloration degree, in a case where a reagent having bleaching action is held in the test strip and in a case where the reagent is not held. FIG. 15(a) shows a quantitative performance in a case where a biosensor which does not include sodium percarbonate as the bleaching reagent is employed and FIG. 15(b) shows a quantitative performance in a case where a biosensor which is provided with the bleaching reagent hold region is employed. The abscissa represents the hCG concentration of a sample applied to the test strip. The ordinate represents the converted value of the hCG concentration in the sample obtained by substituting a signal from a marker in the color area on the test strip into the calibration curve.

Essentially, when for example the absorbance of blood including hCG of 1000 U/l was measured and the measured absorbance was substituted into the calibration curve, the hCG concentration should be 1000 U/l. However, hCG concentration actually deviates slightly. The accuracy of measurement can be known by the amount of the deviation.

Hereinafter, descriptions will be given of a case where the bleaching reagent is not employed and a case where the bleaching reagent hold region is provided on the test strip in a chromatography quantitative measurement with whole blood as a sample.

FIG. 15 show the result obtained by converting the concentration of an analysis target on the basis of a measured value of a coloration degree, five minutes after a whole blood sample is applied to the immunochromatographic test strip. The marker reagent used at this time is the same antibody—gold colloid complex both in FIGS. 15(a) and 15(b). In a case where the bleaching reagent is included in the test strip (FIG. 15(b)), a CV value (coefficient of variation) is within 0 to 15%, while in a case where the bleaching reagent is not included (FIG. 15(a)), the CV value ranges from 20 to 65% having a wide range of variations affected by a pigment of blood corpuscles, and has a low quantitative performance.

From the above results, it can be understood that the incorporation of the bleaching reagent into the biosensor suppresses the effect of the blood-derived pigment, thereby enhancing the quantitative performance.

While in this example the description has been given of the result when sodium percarbonate is employed as the bleaching reagent and potassium chloride is employed as the cellular component contraction agent, others having the bleaching effect and the cell contraction effect may be also employed.

Further, the test strip which is made of chromatography materials composed of an arbitrary porous support body such as nitrocellulose and glass fiber filter paper is employed as the chromatography measuring device in this example. The test strip made of these materials analyzes, detects and qualitatively or quantitatively measures specific substance employing an arbitrary measurement principle such as an antigen antibody reaction. While the description has been given taking the antigen antibody reaction that employs the marker as an example, anything that produces some change before and after the reaction, such as an enzyme, may be employed.

APPLICABILITY IN INDUSTRY

As described above, according to a biosensor of the present invention, no particular device is required, an inspection target solution is only applied without being pretreated previously, an effect of a component of a pigment, such as a blood pigment, which is derived from the inspection target solution is reduced, and an analysis result can be confirmed visually, and particularly the biosensor according to the present invention is suitable for an analysis of a liquid sample including colored components typified by constituents of blood.

The invention claimed is:

1. A biosensor comprising a development layer where an inspection target solution is developed, said biosensor holding at least, a marker reagent part where a marker reagent is held so as to be dissolved by the development of the inspection target solution in a part of the development layer, and a reagent immobilization part where a reagent which specifically reacts to an analysis target in the inspection target solution is immobilized in a part of the development layer, which part is chromatographically downstream relative to the marker reagent part, wherein the development layer is provided with areas where a cellular component contraction agent and a bleaching reagent having bleaching action for fading colored components in a liquid sample are supported respectively so as to be dissolved, at least in parts of downstream of a sample application area where the inspection target solution is applied, in the direction of the inspection target solution permeating.

2. The biosensor as defined in claim 1, wherein the development layer is made of nitrocellulose.

3. The biosensor as defined in claim 1, wherein the bleaching reagent having bleaching action for fading colored components in a liquid sample is directly supported on the development layer so as to be dissolved.

4. The biosensor as defined in claim 1, wherein a sample inflow area to which the inspection target solution flows in by a capillary phenomenon is arranged on the development layer, and the bleaching reagent area is held in the sample inflow area.

5. The biosensor as defined in claim 1, wherein a mixed reagent of the cellular component contraction agent and the reagent having bleaching action is carried in the development layer.

6. The biosensor as defined in claim 1, wherein a space is arranged on the development layer, through which the inspection target solution, getting contact therewith, flows in by a capillary phenomenon, and a mixed cellular component contraction agent and reagent having bleaching action are held in the space in a dry state where it can be dissolved by the inflow of the inspection target solution.

7. The biosensor as defined in claim 1, wherein the inspection target solution to be applied is whole blood.

8. The biosensor as defined in claim 1, wherein the bleaching reagent having bleaching action for fading colored components in a liquid sample is sodium percarbonate.

9. The biosensor as defined in claim 1, wherein the reagent having bleaching action is hydrogen peroxide.

10. The biosensor as defined in claim 1, wherein the reagent having bleaching action is sodium hypochlorite.

11. The biosensor as defined in claim 1, wherein the cellular component contraction agent is inorganic salt.

12. The biosensor as defined in claim 1, wherein the cellular component contraction agent is an amino acid.

13. The biosensor as defined in claim 1, wherein the cellular component contraction agent is a saccharide.

14. The biosensor as defined in claim 1, wherein the biosensor is a one-step immunochromatographic test strip.

15. The biosensor as defined in claim 1, wherein the biosensor is a dry analysis element.

* * * * *